US012127839B2

(12) United States Patent
Neumann

(10) Patent No.: US 12,127,839 B2
(45) Date of Patent: Oct. 29, 2024

(54) SYSTEM AND METHOD FOR GENERATING A STRESS DISORDER RATION PROGRAM

(71) Applicant: KPN INNOVATIONS, LLC., Lakewood, CO (US)

(72) Inventor: Kenneth Neumann, Lakewood, CO (US)

( * ) Notice: Subject to any disclaimer, the term of this patent is extended or adjusted under 35 U.S.C. 154(b) by 232 days.

(21) Appl. No.: 17/243,653

(22) Filed: Apr. 29, 2021

(65) Prior Publication Data

US 2022/0346681 A1    Nov. 3, 2022

(51) Int. Cl.
| | |
|---|---|
| *A61B 5/16* | (2006.01) |
| *G16H 20/60* | (2018.01) |
| *G16H 20/70* | (2018.01) |
| *G16H 50/20* | (2018.01) |

(52) U.S. Cl.
CPC ............ *A61B 5/165* (2013.01); *G16H 20/60* (2018.01); *G16H 20/70* (2018.01); *G16H 50/20* (2018.01)

(58) Field of Classification Search
CPC .......... A61B 5/168; A61B 5/165; A61B 5/16; G16H 50/20; G16H 20/60; G16H 20/70
See application file for complete search history.

(56) References Cited

U.S. PATENT DOCUMENTS

| | | | | |
|---|---|---|---|---|
| 10,553,316 | B1 * | 2/2020 | Neumann | G06N 20/00 |
| 10,553,319 | B1 * | 2/2020 | Neumann | G16H 50/20 |
| 10,559,386 | B1 * | 2/2020 | Neumann | G16B 20/00 |
| 10,593,431 | B1 * | 3/2020 | Neumann | G16H 20/00 |
| 11,074,495 | B2 * | 7/2021 | Zadeh | G06V 40/171 |
| 11,195,057 | B2 * | 12/2021 | Zadeh | G06N 3/006 |
| 11,328,796 | B1 * | 5/2022 | Jain | G16H 10/20 |
| 11,456,080 | B1 * | 9/2022 | Jain | A61B 5/4815 |
| 2013/0031107 | A1 * | 1/2013 | Pan | G06F 16/435 |
| | | | | 707/749 |

(Continued)

FOREIGN PATENT DOCUMENTS

| | | | | |
|---|---|---|---|---|
| CA | 2538758 C | * 10/2014 | ........... | A61B 5/0002 |
| JP | 2018505759 A | * 3/2018 | | |

(Continued)

OTHER PUBLICATIONS

Type: PDF, Frontiers in Molecular Biosciences Title: Biomarkers in Stress Related Diseases/Disorders: Diagnostic, Prognostic, and Therapeutic Values By: Kuldeep Dhama Date: Oct. 18, 2019.

(Continued)

*Primary Examiner* — Kenneth Bartley
(74) *Attorney, Agent, or Firm* — Caldwell Intellectual Property Law

(57) ABSTRACT

A system for generating a stress disorder ration program includes a computing device configured to obtain a stress representation, ascertain an equanimity signature, wherein ascertaining the equanimity signature further comprises retrieving an acclimation element, determining a relative vector as a function of the acclimation element, and ascertaining the equanimity signature as a function of the relative vector and the stress representation using a stress machine-learning model, identify a physiological influence as a function of the equanimity signature, determine an edible as a function of the physiological influence, and generate a ration program as a function of the edible.

20 Claims, 7 Drawing Sheets

(56) References Cited

U.S. PATENT DOCUMENTS

| | | | |
|---|---|---|---|
| 2013/0216989 A1* | 8/2013 | Cuthbert | A61B 5/1113 |
| | | | 434/238 |
| 2017/0188927 A1* | 7/2017 | Nakashima | A61B 5/0295 |
| 2017/0367651 A1* | 12/2017 | Tzvieli | A61B 5/0075 |
| 2018/0239873 A1* | 8/2018 | Eda | G16H 70/60 |
| 2019/0209022 A1* | 7/2019 | Sobol | A61B 5/0022 |
| 2020/0118665 A1* | 4/2020 | Bender | G06N 3/08 |
| 2020/0303074 A1* | 9/2020 | Mueller-Wolf | A61B 5/7275 |
| 2021/0202067 A1* | 7/2021 | Williams | A61B 5/0022 |
| 2021/0319887 A1* | 10/2021 | Derrick, Jr. | A61B 5/7275 |
| 2021/0319894 A1* | 10/2021 | Sobol | G06N 5/01 |
| 2022/0245354 A1* | 8/2022 | Mackay | G10L 25/57 |
| 2023/0144166 A1* | 5/2023 | Alford | G06N 5/022 |
| | | | 706/12 |

FOREIGN PATENT DOCUMENTS

| | | | | |
|---|---|---|---|---|
| JP | 2020099367 A | * | 7/2020 | A61B 5/18 |
| JP | 7203473 B1 | * | 1/2023 | |

OTHER PUBLICATIONS

Type: PDF, Health Psychology Open Title: Best practices for stress measurement: How to measure psychological stress in health research By: Alexandra D Crosswell Date: Dec. 2020.

\* cited by examiner

SYSTEM AND METHOD FOR GENERATING A STRESS DISORDER RATION PROGRAM

FIELD OF THE INVENTION

The present invention generally relates to the field of artificial intelligence. In particular, the present invention is directed to a system and method for generating a stress disorder ration program.

BACKGROUND

Current edible suggestion systems do not account for the level of stress and/or anxiety of an individual. This leads to inefficiency of an edible suggestion system and a poor nutrition plan for the individual. This is further complicated by a lack of uniformity of nutritional plans, which results in dissatisfaction of individuals.

SUMMARY OF THE DISCLOSURE

In an aspect, a system for generating a stress disorder ration program includes a computing device configured to obtain a stress representation, ascertain an equanimity signature, wherein ascertaining the equanimity signature further comprises retrieving an acclimation element, determining a relative vector as a function of the acclimation element, and ascertaining the equanimity signature as a function of the relative vector and the stress representation using a stress machine-learning model, identify a physiological influence as a function of the equanimity signature, determine an edible as a function of the physiological influence, and generate a ration program as a function of the edible.

In another aspect, a method for generating a stress disorder ration program includes obtaining, by a computing device, a stress representation, ascertaining, by the computing device, an equanimity signature, wherein ascertaining the equanimity signature further comprises retrieving an acclimation element, determining a relative vector as a function of the acclimation element, and ascertaining the equanimity signature as a function of the relative vector and the stress representation using a stress machine-learning model, identifying, by the computing device, a physiological influence as a function of the equanimity signature, determining, by the computing device, an edible as a function of the physiological influence, and generating, by the computing device, a ration program as a function of the edible.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for generating a stress disorder ration program. In an embodiment, this disclosure can be used to obtain a stress representation of an individual. Aspects of the present disclosure can be used to ascertain an equanimity signature. This is so, at least in part, because the disclosure utilizes a machine-learning model. Aspects of the present disclosure can also be used to identify a physiological influence and determine an edible as a function of the physiological influence. Aspects of the present disclosure allow for generating a ration program as a function of the edible. Exemplary embodiments illustrating aspects of the present disclosure are described below in the context of several specific examples.

Figure 1:
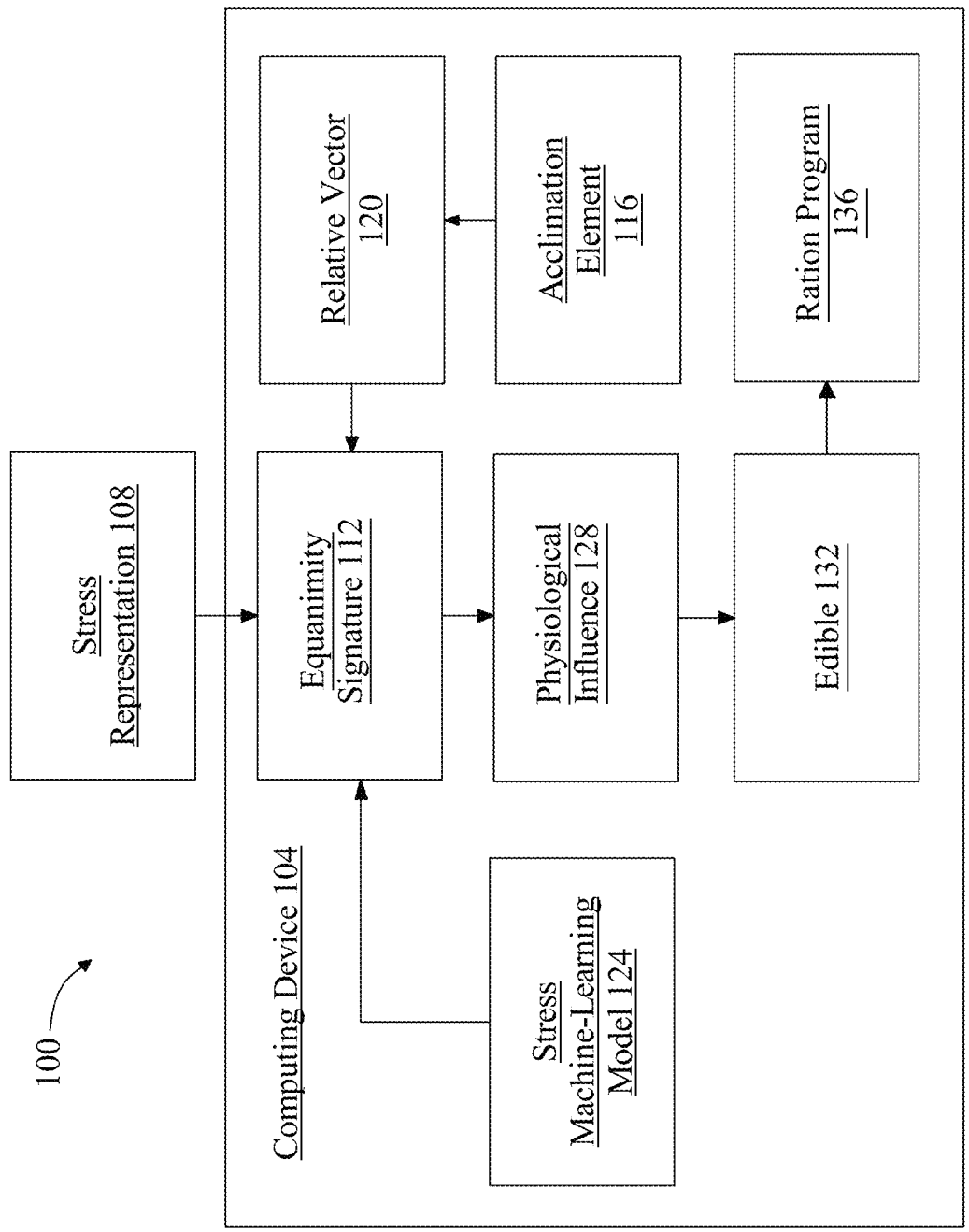
FIG. 1 is a block diagram illustrating an exemplary embodiment of a system for generating a stress disorder ration program.

Referring now to FIG. 1, an exemplary embodiment of a system 100 for generating a stress disorder ration program is illustrated. System includes a computing device 104. computing device 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. computing device 104 may include a single computing device operating independently, or may include two or more computing device operating in concert, in parallel, sequentially or the like; two or more computing devices may be included together in a single computing device or in two or more computing devices. computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. computing device 104 may include but is not limited to, for example, a computing device or cluster of computing devices in a first location and a second computing device or cluster of computing devices in a second location. computing device 104 may include one or more computing devices dedicated to data storage, security, distribution of traffic for load balancing, and the like. computing device 104 may distribute one or more computing tasks as described below across a plurality of computing devices of computing device, which may operate in parallel, in series, redundantly, or in any other manner used for distribution of tasks or memory between computing devices. computing device 104 may be implemented using a "shared nothing" architecture in which data is cached at the worker, in an embodiment, this may enable scalability of system 100 and/or computing device.

With continued reference to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, computing device 104 obtains a stress representation 108. As used in this disclosure a "stress representation" is an element of data representing a measurable value of stress of an individual's biological system, wherein "stress," as used herein, is a physical, emotional, and/or psychological strain exerted on an individual's biological system due to a stimulus. In an embodiment, and without limitation, stress representation may denote a health status of the individual, wherein a health status is a measure of the relative level of physical, social and/or behavioral well-being. In another embodiment, stress representation may denote one or more health statuses of an individual's nervous system, circulatory system, musculoskeletal system, respiratory system, endocrine system, integumentary system, lymphatic system, digestive system, urinary system, reproductive system, and the like thereof. In another embodiment stress representation 108 may indicate that a user is interacting with a stressor. As used in this disclosure a "stressor" is a compound and/or external stimulus that causes stress to an individual. For example, and without limitation, stressor may include a chemical agent, biological agent, environmental condition, external stimulus, and the like thereof. In an embodiment and without limitation, stress representation 108 may include a biological sample. As used in this disclosure a "biological sample" is one or more biological specimens collected from an individual. Biological sample may include, without limitation, exhalate, blood, sputum, urine, saliva, feces, semen, and other bodily fluids, as well as tissue. Stress representation 108 may include a biological sampling device. Stress representation 108 may include one or more biomarkers. As used in this disclosure a "biomarker" is a molecule and/or chemical that identifies the status of an individual's health system and/or stress of an individual's health system. As a non-limiting example, biomarkers may include cortisol, DHEA, epinephrine, norepinephrine, salivary alpha-amylase, pro-inflammatory cytokines, anti-inflammatory cytokines, c-reactive protein, metal ions, NADPH, P450, cyclooxygenase, lipo-oxygenase, glutathione, catalase, superoxide dismutase, glutathione peroxidase, ascorbic acid, vitamin E, and the like thereof. As a further non-limiting example, stress representation 108 may include datum from one or more devices that collect, store, and/or calculate one or more lights, voltages, currents, sounds, chemicals, pressures, and the like thereof that are associated with the individual's health status. For example, and without limitation a device may include a magnetic resonance imaging device, magnetic resonance spectroscopy device, x-ray spectroscopy device, computerized tomography device, ultrasound device, electroretinogram device, electrocardiogram device, ABER sensor, mass spectrometer, and the like thereof.

Still referring to FIG. 1, computing device 104 may obtain stress representation 108 by receiving a medical input. As used in this disclosure a "medical input" is an element of datum that is obtained relating to the stress of an individual. As a non-limiting example, medical input may include a questionnaire and/or survey that identifies a feeling of pain, headache, fever, lethargy, loss of appetite, tenderness, malaise, redness, muscle weakness, and the like thereof. Medical input may include data from an informed advisor as a function of a medical assessment, wherein a "medical assessment" is an evaluation and/or estimation of stress of an individual. As used in this disclosure "informed advisor" is an individual that is skilled in the health and wellness field. As a non-limiting example an informed advisor may include a medical professional who may assist and/or participate in the medical treatment of an individual's health status including, but not limited to psychiatrists, psychologists, endocrinologist, psychotherapists, family physicians, gastroenterologists, internists, oncologists, pediatricians, cardiologists, geneticists, neurologists, physical therapists, primary care providers, and the like thereof. As a non-limiting example, medical input may include an informed advisor that enters a medical assessment comprising a physical exam, neurologic exam, blood test, urine test, imaging test, cellular and/or chemical analysis, genetic test, measurement, visual examination, and the like thereof. As a further non-limiting example, medical input may include one or more inputs from a family member. For example, and without limitation, a brother, sister, mother, father, cousin, aunt, uncle, grandparent, child, friend, and the like thereof may enter to computing device 104 that an individual is experiencing stress.

Still referring to FIG. 1, stress representation 108 may include one or more representations of stress as a function of a psychological analysis. As used in this disclosure a "psychological analysis" is an evaluation and/or estimation of the cognitive functions of an individual. For example, and without limitation, a psychological analysis may include one or more assessments of memory, behavior, motor function, emotions, and the like thereof. Psychological analysis may identify one or more feelings and/or cognitive functions of an individual such as, but not limited to, feeling nervous, on edge, restless, unsettled, stressed, surprised, creative, imaginative, daring, adventurous, high energy, low energy, angry, calm, comfortable, contentment, peace, relaxed, loveable, slow moving, fast moving, irritable, impulsive, dull, obsessing, and the like thereof. Psychological analysis may additionally or alternatively include any psychological analysis used as a psychological analysis as described in U.S. Nonprovisional application Ser. No. 17/128,120, filed on Dec. 29, 2020, and entitled "METHODS AND SYSTEMS FOR NOURISHMENT REFINEMENT USING PSYCHIATRIC MARKERS," the entirety of which is incorporated herein by reference.

In an embodiment, and still referring to FIG. 1, computing device 104 may obtain stress representation 108 as a function of retrieving a behavior pattern. As used in this disclosure a "behavior pattern" is a habit and/or repeated action of the individual that leads to a modified amount of stress. For example, and without limitation behavior pattern may include one or more habits and/or actions such as sleeping too little, eating an unhealthy diet, forgoing fitness, emotional distancing, consuming excessive caffeine, consuming excessive alcohol, scrolling through social media, and the like thereof. In an embodiment, and without limitation, behavior pattern may include a stress mitigator. As used in this disclosure a "stress mitigator" is an action and/or behavior that aids in reducing stress and/or eliminating a stressor. For example, and without limitation, stress mitigator may include one or more habits and/or actions such as daily exercise, eating a healthy diet, reducing caffeine intake, participating in a sport, breathing exercises, and the like thereof.

Still referring to FIG. 1, computing device 104 ascertains an equanimity signature 112. As used in this disclosure an "equanimity signature" is a representation and/or profile of the magnitude of stress of an individual. For example, and without limitation, equanimity signature 112 may denote that a magnitude of stress of an individual is exhibiting exceeds a predicted and/or expected magnitude of stress that should be experienced. As a further non-limiting example, equanimity signature 112 may denote that a magnitude of stress an individual is exhibiting is abnormally low compared to a predicted and/or expected magnitude of stress that should be experienced. Computing device 104 ascertains equanimity signature 112 as a function of retrieving an acclimation element 116. As used in this disclosure an "acclimation element" is an element of datum denoting an acclimation and/or experience with a stressful situation and/or a stressor. As used in this disclosure a "stressful situation" is an event and/or experience that causes an individual to feel and/or experience stress, wherein stress is defined above in detail. For example, and without limitation, acclimation element 116 may denote that an individual is used to hearing firearm discharges and/or loud noises as a function of growing up and/or frequenting a firearm training facility, wherein that individual may have a reduced stress when hearing a loud noise and/or firearm discharge. As a further non-limiting example, acclimation element 116 may denote that an individual is used to interactions with law enforcement officers as a function of volunteering as a first responder, wherein an interaction with a law enforcement officer may result in reduced stress on the individual's body when interacting with a law enforcement officer. As a further non-limiting example, acclimation element may denote that an individual has no previous experience and/or history interacting with animals, wherein that individual may have an elevated effect of stress due to an incident, such as a bite, with a canine.

Still referring to FIG. 1, computing device 104 determines a relative vector 120 as a function of acclimation element 116. As used in this disclosure a "relative vector" is a data structure that represents one or more quantitative values and/or measures of relative stress of an individual for a given stressful event and/or stressor. For example, and without limitation, relative vector 120 may be a value of 30 for a stressor of a high stress job, wherein the individual has 20 years of experience working at the high stress job. As a further non-limiting example, relative vector 120 may be a value of 80 for a stressor of need a surgery, wherein the individual has never had experienced a surgical procedure. A vector may be represented as an n-tuple of values, where n is one or more values, as described in further detail below; a vector may alternatively or additionally be represented as an element of a vector space, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm: $l=\sqrt{\sum_{i=0}^{n} a_i^2}$, where $a_i$ is attribute number i of the vector. Scaling and/or normalization may function to make vector comparison independent of absolute quantities of attributes, while preserving any dependency on similarity of attributes.

In an embodiment, and without limitation, computing device 104 may determine relative vector 120 as a function of retrieving an expected response. As used in this disclosure an "expected response" is a response to a stimulus and/or stressor that is expected and/or predicted. For example, and without limitation, expected response associated with a career change may include elevated heart rate, muscle aches, insomnia, and the like thereof. As a further non-limiting example, expected response associated with a death of a loved one may include avoidance, nail biting, decreased appetite, numbness, and the like thereof. In an embodiment, expected response may be retrieved from one or more medical databases. As used in this disclosure a "medical database" is a database containing one or more expected responses. Medical database may be implemented, without limitation, as a relational databank, a key-value retrieval databank such as a NOSQL databank, or any other format or structure for use as a databank that a person skilled in the art would recognize as suitable upon review of the entirety of this disclosure. Medical database may alternatively or additionally be implemented using a distributed data storage protocol and/or data structure, such as a distributed hash table or the like. Medical database may include a plurality of data entries and/or records as described above. Data entries in a databank may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a databank may store, retrieve, organize, and/or reflect data and/or records as used herein, as well as categories and/or populations of data consistently with this disclosure. Medical database may include a peer review. Peer review may identify one or more expected responses as a function of a peer review evaluation conducted by one or more informed advisors with similar competencies. As a non-limiting example peer review may include professional peer reviews, scholarly peer reviews, government peer reviews, medical peer reviews, technical peer reviews, and the like thereof. Medical database may include an informed advisor association. Informed advisor association may identify one or more expected responses as a function of one or more committees, organizations, and/or groups. As a non-limiting example informed advisor association may include the such as the American Medical Association, American Psychiatric Association, American Red Cross, Anxiety and Depression Association of America, American Academy of Experts in Traumatic Stress, American Psychological Association, American Academy of Child and Adolescent Psychiatry, and the like thereof. Medical database may include a medical website. Medical website may identify one or more expected responses as a function of one or more online and/or web-based medical recommendations. As a non-limiting example medical website may include Medline Plus, Drugs.com, Mayo Clinic, Orphanet, Medgadget, WebMD, Health.gov, SPM ePatients blog, and the like thereof.

Still referring to FIG. 1, computing device 104 may determine relative vector 120 as a function of acclimation element 116 and expected response using a relative machine-learning model As used in this disclosure "relative machine-learning model" is a machine-learning model to produce a relative vector output given acclimation elements and expected responses as inputs; this is in contrast to a non-machine learning software program where the commands to be executed are determined in advance by a user and written in a programming language. Relative machine-learning model may include one or more relative machine-learning processes such as supervised, unsupervised, or reinforcement machine-learning processes that computing device 104 and/or a remote device may or may not use in the determination of relative vector 120. As used in this disclosure "remote device" is an external device to computing device 104. Relative machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train relative machine-learning process as a function of a relative training set. As used in this disclosure "relative training set" is a training set that correlates an acclimation element and/or expected response to a relative vector. For example, and without limitation, an acclimation element of being an electrician for 20 years and an expected response of muscular contraction due to accidental DC shock may relate to a relative vector 20 for an elongated muscular contraction response. The relative training set may be received as a function of user-entered valuations of acclimation elements, expected responses, and/or relative vectors. Computing device 104 may receive relative training set by receiving correlations of acclimation elements, and/or expected responses that were previously received and/or determined during a previous iteration of determining relative vectors. The relative training set may be received by one or more remote devices that at least correlate an acclimation element and/or expected response to a relative vector. The relative training set may be received in the form of one or more user-entered correlations of an acclimation element and/or expected response to a relative vector. Additionally or alternatively, a user may include an informed advisor, wherein an informed advisor may include, without limitation, psychiatrists, psychologists, endocrinologist, psychotherapists, family physicians, gastroenterologists, internists, oncologists, pediatricians, cardiologists, geneticists, neurologists, physical therapists, primary care providers, and the like thereof.

Still referring to FIG. 1, computing device 104 may receive relative machine-learning model from a remote device that utilizes one or more relative machine learning processes, wherein a remote device is described above in detail. For example, and without limitation, a remote device may include a computing device, external device, processor, and the like thereof. Remote device may perform the relative machine-learning process using the relative training set to generate relative vector 120 and transmit the output to computing device 104. Remote device may transmit a signal, bit, datum, or parameter to computing device 104 that at least relates to relative vector 120. Additionally or alternatively, the remote device may provide an updated machine-learning model. For example, and without limitation, an updated machine-learning model may be comprised of a firmware update, a software update, a relative machine-learning process correction, and the like thereof. As a non-limiting example a software update may incorporate a new acclimation element that relates to a modified expected response. Additionally or alternatively, the updated machine learning model may be transmitted to the remote device, wherein the remote device may replace the relative machine-learning model with the updated machine-learning model and determine the relative vector as a function of the acclimation element using the updated machine-learning model. The updated machine-learning model may be transmitted by the remote device and received by computing device 104 as a software update, firmware update, or corrected relative machine-learning model. For example, and without limitation relative machine-learning model 120 may utilize a random forest machine-learning process, wherein the updated machine-learning model may incorporate a gradient boosting machine-learning process. Updated machine learning model may additionally or alternatively include any machine-learning model used as an updated machine learning model as described in U.S. Nonprovisional application Ser. No. 17/106,658, filed on Nov. 30, 2020, and entitled "A SYSTEM AND METHOD FOR GENERATING A DYNAMIC WEIGHTED COMBINATION," the entirety of which is incorporated herein by reference.

Still referring to FIG. 1, computing device 104 may determine relative vector 120 as a function of a classifier. A "classifier," as used in this disclosure is a machine-learning model, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Computing device 104 and/or another device may generate a classifier using a classification algorithm, defined as a processes whereby a computing device 104 derives a classifier from training data. Classification may be performed using, without limitation, linear classifiers such as without limitation logistic regression and/or naïve Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

Still referring to FIG. 1, computing device 104 may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A) P(A)\div P(B)$, where $P(A/B)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Computing device 104 may then calculate a likelihood table by calculating probabilities of different data entries and classification labels. Computing device 104 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 1, computing device 104 may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 1, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least one value. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute/as derived using a Pythagorean norm: $l=\sqrt{\sum_{i=0}^{n} a_i^2}$, where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

Still referring to FIG. 1, computing device 104 ascertains equanimity signature 112 as a function of relative vector 120 and stress representation 108 using a stress machine-learning model 124. As used in this disclosure "stress machine-learning model" is a machine-learning model to produce an equanimity signature output given relative vectors and stress representations as inputs; this is in contrast to a non-machine learning software program where the commands to be executed are determined in advance by a user and written in a programming language. Stress machine-learning model 124 may include one or more stress machine-learning processes such as supervised, unsupervised, or reinforcement machine-learning processes that computing device 104 and/ or a remote device may or may not use in the determination of equanimity signature 112, wherein a remote device is described above in detail. Stress machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train stress machine-learning process as a function of a stress training set. As used in this disclosure "stress training set" is a training set that correlates a relative vector and/or stress representation to an equanimity signature. For example, and without limitation, a relative vector of an 80 for being stuck in a small space and a stress representation of loss of cognitive memory may relate to an equanimity signature of excessive stress experienced by the individual. The stress training set may be received as a function of user-entered valuations of relative vectors, stress representations, and/or equanimity signatures. Computing device 104 may receive stress training set by receiving correlations of relative vectors, and/or stress representations that were previously received and/or determined during a previous iteration of determining equanimity signatures. The stress training set may be received by one or more remote devices that at least correlate a relative vector and/or stress representation to an equanimity signature. The stress training set may be received in the form of one or more user-entered correlations of a relative vector and/or stress representation to an equanimity signature. Additionally or alternatively, a user may include an informed advisor, wherein an informed advisor may include, without limitation, psychiatrists, psychologists, endocrinologist, psychotherapists, family physicians, gastroenterologists, internists, oncologists, pediatricians, cardiologists, geneticists, neurologists, physical therapists, primary care providers, and the like thereof.

Still referring to FIG. 1, computing device 104 may receive stress machine-learning model 124 from a remote device that utilizes one or more stress machine learning processes, wherein a remote device is described above in detail. For example, and without limitation, a remote device may include a computing device, external device, processor, and the like thereof. Remote device may perform the stress machine-learning process using the stress training set to generate equanimity signature 112 and transmit the output to computing device 104. Remote device may transmit a signal, bit, datum, or parameter to computing device 104 that at least relates to equanimity signature 112. Additionally or alternatively, the remote device may provide an updated machine-learning model. For example, and without limitation, an updated machine-learning model may be comprised of a firmware update, a software update, a stress machine-learning process correction, and the like thereof. As a non-limiting example a software update may incorporate a new relative vector that relates to a modified stress representation. Additionally or alternatively, the updated machine learning model may be transmitted to the remote device, wherein the remote device may replace the stress machine-learning model with the updated machine-learning model and determine the equanimity signature as a function of the relative vector using the updated machine-learning model. The updated machine-learning model may be transmitted by the remote device and received by computing device 104 as a software update, firmware update, or corrected stress machine-learning model. For example, and without limitation stress machine-learning model 112 may utilize a random forest machine-learning process, wherein the updated machine-learning model may incorporate a gradient boosting machine-learning process. Updated machine learning model may additionally or alternatively include any machine-learning model used as an updated machine learning model as described in U.S. Nonprovisional application Ser. No. 17/106,658, the entirety of which is incorporated herein by reference. In an embodiment, and without limitation, stress machine-learning model may identify equanimity signature as a function of one or more classifiers, wherein a classifier is described above in detail.

In an embodiment, and still referring to FIG. 1, computing device 104 may ascertain equanimity signature 112 as a function of identifying a likelihood element. As used in this disclosure a "likelihood element" is an element of data that represents one or more probabilities for experiencing a large magnitude of stress. For example, and without limitation, likelihood element may denote that an individual has a propensity for elevated stress due to experiencing intense and/or long-lasting trauma previously. As a further non-limiting example, likelihood element may denote that an individual has a propensity for elevated stress due to being the victim of child abuse. As a further non-limiting example, likelihood element may denote that an individual has a propensity for elevated stress because the individual has a job that exposes the individual to traumatic events such as, but not limited to, military personnel and/or first responders. As a further non-limiting example, likelihood element may denote that an individual has a propensity for elevated stress because the individual suffers from a mental health disorder. As a further non-limiting example, likelihood element may denote that an individual has a propensity for elevated stress due to a substance abuse disorder. As a further non-limiting example, likelihood element may denote that an individual has a propensity for elevated stress because the individual has relatives that experience large magnitudes of stress.

Still referring to FIG. 1, computing device 104 may produce equanimity signature 112 by identifying a stress disorder. As used in this disclosure a "stress disorder" is an ailment and/or collection of ailments that impact an individual's health status. As a non-limiting example stress disorder may include social anxiety disorder, post-traumatic stress disorder, panic disorder, generalized anxiety disorder, agoraphobia, selective mutism, separation anxiety disorder, stress induced anxiety disorder, and the like thereof. Stress disorder may be identified as a function of one or more disorder machine-learning models. As used in this disclosure a "disorder machine-learning model" is a machine-learning model to produce a stress disorder output given stress representations as inputs; this is in contrast to a non-machine learning software program where the commands to be executed are determined in advance by a user and written in a programming language. Disorder machine-learning model may include one or more disorder machine-learning processes such as supervised, unsupervised, or reinforcement machine-learning processes that computing device 104 and/or a remote device may or may not use in the determination of stress disorder. A disorder machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train disorder machine-learning process as a function of a disorder training set. As used in this disclosure "disorder training set" is a training set that correlates a stress representation to a stress disorder. As a non-limiting example a stress representation of an elevated concentration of cortisol may relate to a stress disorder of post-traumatic stress disorder. The disorder training set may be received as a function of user-entered valuations of stress representations and/or stress disorders. Computing device 104 may receive disorder training by receiving correlations of stress representations and/or stress disorders that were previously received and/or determined during a previous iteration. The disorder training set may be received by one or more remote devices that at least correlate stress representations to stress disorders, wherein a remote device is an external device to computing device 104, as described above. The disorder training set may be received by one or more user-entered correlations of stress representations to stress disorders. Additionally or alternatively, a user may include an informed advisor, wherein an informed advisor may include, without limitation, psychiatrists, psychologists, endocrinologist, psychotherapists, family physicians, gastroenterologists, internists, oncologists, pediatricians, cardiologists, geneticists, neurologists, physical therapists, primary care providers, and the like thereof.

Still referring to FIG. 1, computing device 104 may receive disorder machine-learning model from a remote device that utilizes one or more disorder machine learning processes, wherein a remote device is described above in detail. For example, and without limitation, a remote device may include a computing device, external device, processor, and the like thereof. Remote device may perform the disorder machine-learning process using the disorder training set to generate stress disorder and transmit the output to computing device 104. Remote device may transmit a signal, bit, datum, or parameter to computing device 104 that at least relates to stress disorders. Additionally or alternatively, the remote device may provide an updated machine-learning model. For example, and without limitation, an updated machine-learning model may be comprised of a firmware update, a software update, a disorder machine-learning process correction, and the like thereof. As a non-limiting example a software update may incorporate a new stress representation that relates to a modified stress disorder. Additionally or alternatively, the updated machine learning model may be transmitted to the remote device, wherein the remote device may replace the disorder machine-learning model with the updated machine-learning model and determine the stress disorder as a function of the stress representation using the updated machine-learning model. The updated machine-learning model may be transmitted by the remote device and received by computing device 104 as a software update, firmware update, or corrected disorder machine-learning model. For example, and without limitation disorder machine-learning model may utilize a neural net machine-learning process, wherein the updated machine-learning model may incorporate hierarchical clustering machine-learning process. Updated machine learning model may additionally or alternatively include any machine-learning model used as an updated machine learning model as described in U.S. Nonprovisional application Ser. No. 17/106,658, the entirety of which is incorporated herein by reference. In an embodiment, and without limitation, disorder machine-learning model may identify stress disorder as a function of one or more classifiers, wherein a classifier is described above in detail.

Still referring to FIG. 1, computing device identifies a physiological influence 128 as a function of equanimity signature 112. As used in this disclosure a "physiological influence" is an effect and/or influence that equanimity signature and/or stress representation has on an individual's body. For example, and without limitation, physiological influence 128 may include one or more psychological symptoms including, but not limited to, becoming easily agitated, frustration, difficulty relaxing, low energy, headaches, upset stomach, tense muscles, chest pains, rapid heart rate, insomnia, nervousness, tinnitus, dry mouth, difficulty swallowing, memory loss, cardiovascular disease, obesity, sexual dysfunction, acne, psoriasis, eczema, gastrointestinal problems, and the like thereof. In an embodiment, and without limitation, physiological influence 128 may be identified as a function of determining an influence group, wherein an influence group is a group representing one or more types of influences that effect the individual's body as described below in detail, in reference to FIG. 3. For example, and without limitation, influence group may denote one or more acute groups, episodic acute groups, and/or chronic groups. Computing device 104 may identify physiological influence 128 as a function of receiving at least a stress target tissue, wherein a stress target tissue is one or more tissues and/or cells that are affected by a stressor as described below in detail, in reference to FIG. 2. For example, and without limitation, stress target tissue may be received as a function of one or more one or more medical sources, such as medical textbooks, medical societies, medical organizations, medical websites, and the like thereof. For example, and without limitation, stress target tissue may be received as a function of a medical textbook such as the Diagnostic and Statistical Manual of Mental Disorders, $5^{th}$ Edition: DSM-5. As a further non-limiting example, stress target tissue may be received as a function of a medical website such as WebMD-.com, and/or MayoClinic.org.

Still referring to FIG. 1, physiological influence 128 may be identified as a function of stress target tissue and equanimity signature 112 using a physiological machine-learning model. As used in this disclosure a "physiological machine-learning model" is a machine-learning model to produce a physiological influence output given stress target tissues and equanimity signatures as inputs; this is in contrast to a non-machine learning software program where the commands to be executed are determined in advance by a user and written in a programming language. Physiological machine-learning model may include one or more physiological machine-learning processes such as supervised, unsupervised, or reinforcement machine-learning processes that computing device 104 and/or a remote device may or may not use in the determination of physiological influence 128, wherein a remote device is an external device to computing device 104 as described above in detail. A physiological machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train physiological machine-learning process as a function of a physiological training set. As used in this disclosure a "physiological training set" is a training set that correlates at least stress target tissue and equanimity signature to a physiological influence. For example, and without limitation, stress target tissue of cardiac muscle tissue and an equanimity signature of an enhanced stress magnitude for a stressor may relate to a physiological influence of cardiac infarction. The physiological training set may be received as a function of user-entered valuations of stress target tissues, equanimity signatures, and/or physiological influences. Computing device 104 may receive physiological training set by receiving correlations of stress target tissues and/or equanimity signatures that were previously received and/or determined during a previous iteration of determining physiological influences. The physiological training set may be received by one or more remote devices that at least correlate a stress target tissue and equanimity signature to a physiological influence, wherein a remote device is an external device to computing device 104, as described above. Physiological training set may be received in the form of one or more user-entered correlations of a stress target tissue and/or equanimity signature to a physiological influence. Additionally or alternatively, a user may include an informed advisor, wherein an informed advisor may include, without limitation, psychiatrists, psychologists, endocrinologist, psychotherapists, family physicians, gastroenterologists, internists, oncologists, pediatricians, cardiologists, geneticists, neurologists, physical therapists, primary care providers, and the like thereof.

Still referring to FIG. 1, computing device 104 may receive physiological machine-learning model from a remote device that utilizes one or more physiological machine learning processes, wherein remote device is described above in detail. For example, and without limitation, remote device may include a computing device, external device, processor, and the like thereof. Remote device may perform the physiological machine-learning process using the physiological training set to generate physiological influence 128 and transmit the output to computing device 104. Remote device may transmit a signal, bit, datum, or parameter to computing device 104 that at least relates to physiological influence 128. Additionally or alternatively, the remote device may provide an updated machine-learning model. For example, and without limitation, an updated machine-learning model may be comprised of a firmware update, a software update, a physiological machine-learning process correction, and the like thereof. As a non-limiting example a software update may incorporate a new stress target tissue that relates to a modified equanimity signature. Additionally or alternatively, the updated machine learning model may be transmitted to the remote device, wherein the remote device may replace the physiological machine-learning model with the updated machine-learning model and determine the physiological as a function of the equanimity signature using the updated machine-learning model. The updated machine-learning model may be transmitted by the remote device and received by computing device 104 as a software update, firmware update, or corrected physiological machine-learning model. For example, and without limitation a physiological machine-learning model may utilize a neural net machine-learning process, wherein the updated machine-learning model may incorporate polynomial regression machine-learning process. Updated machine learning model may additionally or alternatively include any machine-learning model used as an updated machine learning model as described in U.S. Nonprovisional application Ser. No. 17/106,658, the entirety of which is incorporated herein by reference. In an embodiment, and without limitation, physiological machine-learning model may identify physiological influence 128 as a function of one or more classifiers, wherein a classifier is described above in detail.

Still referring to FIG. 1, computing device 104 determines an edible 132 as a function of physiological influence 128. As used in this disclosure an "edible" is a source of nourishment that may be consumed by a user such that the user may absorb the nutrients from the source. For example and without limitation, an edible may include legumes, plants, fungi, nuts, seeds, breads, dairy, eggs, meat, cereals, rice, seafood, desserts, dried foods, dumplings, pies, noodles, salads, stews, soups, sauces, sandwiches, and the like thereof. In an embodiment, edible 132 may be determined by identifying at least a nostalgic element, wherein a nostalgic element is an element of datum representing a soothing and/or comforting effect of an edible as described below in detail. For example, and without limitation, nostalgic element may include one or more comfort edibles, such as but not limited to ice cream, doughnuts, cookies, brownies, hamburgers, fries, and the like thereof. Computing device 104 may determine edible 132 as a function of receiving a nourishment composition. As used in this disclosure a "nourishment composition" is a list and/or compilation of all of the nutrients contained in an edible. As a non-limiting example nourishment composition may include one or more quantities and/or amounts of total fat, including saturated fat and/or trans-fat, cholesterol, sodium, total carbohydrates, including dietary fiber and/or total sugars, protein, vitamin A, vitamin C, thiamin, riboflavin, niacin, pantothenic acid, vitamin b6, folate, biotin, vitamin B12, vitamin D, vitamin E, vitamin K, calcium, iron, phosphorous, iodine, magnesium, zinc, selenium, copper, manganese, chromium, molybdenum, chloride, and the like thereof.

In an embodiment, and still referring to FIG. 1, nourishment composition may be obtained as a function of an edible directory, wherein an "edible directory" is a database of edibles that may be identified as a function of one or more metabolic components. Edible directory may be implemented, without limitation, as a relational databank, a key-value retrieval databank such as a NOSQL databank, or any other format or structure for use as a databank that a person skilled in the art would recognize as suitable upon review of the entirety of this disclosure. Edible directory may alternatively or additionally be implemented using a distributed data storage protocol and/or data structure, such as a distributed hash table or the like. Edible directory may include a plurality of data entries and/or records as described above. Data entries in a databank may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a databank may store, retrieve, organize, and/or reflect data and/or records as used herein, as well as categories and/or populations of data consistently with this disclosure. Edible directory may include a carbohydrate tableset. Carbohydrate tableset may relate to a nourishment composition of an edible with respect to the quantity and/or type of carbohydrates in the edible. As a non-limiting example, carbohydrate tableset may include monosaccharides, disaccharides, oligosaccharides, polysaccharides, and the like thereof. Edible directory may include a fat tableset. Fat tableset may relate to a nourishment composition of an edible with respect to the quantity and/or type of esterified fatty acids in the edible. Fat tableset may include, without limitation, triglycerides, monoglycerides, diglycerides, phospholipids, sterols, waxes, and free fatty acids. Edible directory may include a fiber tableset. Fiber tableset may relate to a nourishment composition of an edible with respect to the quantity and/or type of fiber in the edible. As a non-limiting example, fiber tableset may include soluble fiber, such as beta-glucans, raw guar gum, psyllium, inulin, and the like thereof as well as insoluble fiber, such as wheat bran, cellulose, lignin, and the like thereof. Edible directory may include a mineral tableset. Mineral tableset may relate to a nourishment composition of an edible with respect to the quantity and/or type of minerals in the edible. As a non-limiting example, mineral tableset may include calcium, phosphorous, magnesium, sodium, potassium, chloride, sulfur, iron, manganese, copper, iodine, zing, cobalt, fluoride, selenium, and the like thereof. Edible directory may include a protein tableset. Protein tableset may relate to a nourishment composition of an edible with respect to the quantity and/or type of proteins in the edible. As a non-limiting example, protein tableset may include amino acids combinations, wherein amino acids may include, without limitation, alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, and the like thereof. Edible directory may include a vitamin tableset. Vitamin tableset may relate to a nourishment composition of an edible with respect to the quantity and/or type of vitamins in the edible. As a non-limiting example, vitamin tableset may include vitamin A, vitamin $B_1$, vitamin $B_2$, vitamin $B_3$, vitamin $B_5$, vitamin $B_6$, vitamin $B_7$, vitamin $B_9$, vitamin $B_{12}$, vitamin C, vitamin D, vitamin E, vitamin K, and the like thereof.

Still referring to FIG. 1, computing device 104 may produce a nourishment desideration as a function of physiological influence 128. As used in this disclosure a "nourishment desideration" is requirement and/or necessary amount of nutrients required for a user to consume. As a non-limiting example, nourishment desideration may include a user requirement of 35 g of fiber to be consumed per day. Nourishment desideration may be determined as a function of receiving a nourishment goal. As used in this disclosure a "nourishment goal" is a recommended amount of nutrients that a user should consume. Nourishment goal may be identified by one or more organizations that relate to, represent, and/or study stress disorders in humans, such as the American Medical Association, American Psychiatric Association, American Red Cross, Anxiety and Depression Association of America, American Academy of Experts in Traumatic Stress, American Psychological Association, American Academy of Child and Adolescent Psychiatry, and the like thereof.

Still referring to FIG. 1, computing device 104 may identify edible 132 as a function of nourishment composition, nourishment desideration, and an edible machine-learning model. As used in this disclosure a "edible machine-learning model" is a machine-learning model to produce an edible output given nourishment compositions and nourishment desiderations as inputs; this is in contrast to a non-machine learning software program where the commands to be executed are determined in advance by a user and written in a programming language. Edible machine-learning model may include one or more edible machine-learning processes such as supervised, unsupervised, or reinforcement machine-learning processes that computing device 104 and/or a remote device may or may not use in the determination of edible 132, wherein a remote device is an external device to computing device 104 as described above in detail. An edible machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train edible machine-learning process as a function of an edible training set. As used in this disclosure an "edible training set" is a training set that correlates at least nourishment composition and nourishment desideration to an edible. For example, and without limitation, nourishment composition of 100 mg of Omega-3 fatty acids and a nourishment desideration of 90 mg of Omega-3 fatty acids as a function of general anxiety depression may relate to an edible of walnuts. The edible training set may be received as a function of user-entered valuations of nourishment compositions, nourishment desiderations, and/or edibles. Computing device 104 may receive edible training set by receiving correlations of nourishment compositions and/or nourishment desiderations that were previously received and/or determined during a previous iteration of determining edibles. The edible training set may be received by one or more remote devices that at least correlate a nourishment composition and nourishment desideration to an edible, wherein a remote device is an external device to computing device 104, as described above. Edible training set may be received in the form of one or more user-entered correlations of a nourishment composition and/or nourishment desideration to an edible. Additionally or alternatively, a user may include an informed advisor, wherein an informed advisor may include, without limitation psychiatrists, psychologists, endocrinologist, psychotherapists, family physicians, gastroenterologists, internists, oncologists, pediatricians, cardiologists, geneticists, neurologists, physical therapists, primary care providers, and the like thereof.

Still referring to FIG. 1, computing device 104 may receive edible machine-learning model from a remote device that utilizes one or more edible machine learning processes, wherein remote device is described above in detail. For example, and without limitation, remote device may include a computing device, external device, processor, and the like thereof. Remote device may perform the edible machine-learning process using the edible training set to generate edible 132 and transmit the output to computing device 104. Remote device may transmit a signal, bit, datum, or parameter to computing device 104 that at least relates to edible 132. Additionally or alternatively, the remote device may provide an updated machine-learning model. For example, and without limitation, an updated machine-learning model may be comprised of a firmware update, a software update, an edible machine-learning process correction, and the like thereof. As a non-limiting example a software update may incorporate a new nourishment composition that relates to a modified nourishment desideration. Additionally or alternatively, the updated machine learning model may be transmitted to the remote device, wherein the remote device may replace the edible machine-learning model with the updated machine-learning model and determine the edible as a function of the nourishment desideration using the updated machine-learning model. The updated machine-learning model may be transmitted by the remote device and received by computing device 104 as a software update, firmware update, or corrected edible machine-learning model. For example, and without limitation an edible machine-learning model may utilize a neural net machine-learning process, wherein the updated machine-learning model may incorporate polynomial regression machine-learning process. Updated machine learning model may additionally or alternatively include any machine-learning model used as an updated machine learning model as described in U.S. Nonprovisional application Ser. No. 17/106,658, the entirety of which is incorporated herein by reference. In an embodiment, and without limitation, edible machine-learning model may identify edible 132 as a function of one or more classifiers, wherein a classifier is described above in detail.

Still referring to FIG. 1, computing device 104 may identify edible as a function of a likelihood parameter. As used in this disclosure a "likelihood parameter" is a parameter that identities the probability of a user to consume an edible. As a non-limiting example likelihood parameter may identify a high probability that a user will consume an edible of chicken. As a further non-limiting example likelihood parameter may identify a low probability that a user will consume an edible of spinach. Likelihood parameter may be determined as a function of a user taste profile. As used in this disclosure a "user taste profile" is a profile of a user that identifies one or more desires, preferences, wishes, and/or wants that a user has. As a non-limiting example a user taste profile may include a user's preference for cinnamon flavor and/or crunchy textured edibles. Likelihood parameter may be determined as a function of an edible profile. As used in this disclosure an "edible profile" is taste of an edible is the sensation of flavor perceived in the mouth and throat on contact with the edible. Edible profile may include one or more flavor variables. As used in this disclosure a "flavor variable" is a variable associated with the distinctive taste of an edible, wherein a distinctive may include, without limitation sweet, bitter, sour, salty, umami, cool, and/or hot. Edible profile may be determined as a function of receiving flavor variable from a flavor directory. As used in this disclosure a "flavor directory" is a database or other data structure including flavors for an edible. As a non-limiting example flavor directory may include a list and/or collection of edibles that all contain sweet flavor variables. As a further non-limiting example flavor directory may include a list and/or collection of edibles that all contain sour flavor variables. Flavor directory may be implemented similarly to an edible directory as described above in detail. Likelihood parameter may alternatively or additionally include any user taste profile and/or edible profile used as a likelihood parameter as described in U.S. Nonprovisional application Ser. No. 17/032,080, filed on Sep. 25, 2020, and entitled "METHODS, SYSTEMS, AND DEVICES FOR GENERATING A REFRESHMENT INSTRUCTION SET BASED ON INDIVIDUAL PREFERENCES," the entirety of which is incorporated herein by reference.

Still referring to FIG. 1, computing device 104 generates a ration program 136 as a function of edible 132. As used in this disclosure a "ration program" is a program consisting of one or more edibles that are to be consumed over a given time period, wherein a time period is a temporal measurement such as seconds, minutes, hours, days, weeks, months, years, and the like thereof. As a non-limiting example ration program 136 may consist of recommending matcha powder for 8 days. As a further non-limiting example ration program 136 may recommend swiss chard for a first day, sweet potatoes for a second day, and kimchi for a third day. Ration program 136 may include one or more diet programs such as paleo, keto, vegan, vegetarian, Mediterranean, Dukan, Zone, HCG, and the like thereof. Computing device 104 may develop ration program 136 as a function of an intended functional goal. As used in this disclosure an "intended functional goal" is a goal that an edible may generate according to a predicted and/or purposeful plan. As a non-limiting example, intended functional goal may include a treatment goal. As used in this disclosure a "treatment goal" is an intended functional goal that is designed to at least reverse and/or eliminate stress representation 108, equanimity signature 112, physiological influence 128, and/or stress disorder. As a non-limiting example, a treatment goal may include reversing the effects of post-traumatic stress disorder. As a further non-limiting example, a treatment goal includes reversing panic disorder. Intended functional goal may include a prevention goal. As used in this disclosure a "prevention goal" is an intended functional goal that is designed to at least prevent and/or avert stress representation 108, equanimity signature 112, physiological influence 128, and/or stress disorder. As a non-limiting example, a prevention goal may include preventing the development of generalized anxiety disorder. Intended functional goal may include a mitigation goal. As used in this disclosure a "mitigation goal" is a functional goal that is designed to reduce the symptoms and/or effects of stress representation 108, equanimity signature 112, physiological influence 128, and/or stress disorder. For example, and without limitation, mitigation goal may include reducing the effects of social anxiety disorder. Additionally or alternatively, intended functional goal may include one or more goals associated with epigenetic alteration and/or gene therapy to alter a mutation and/or modification associated with a stress disorder.

Still referring to FIG. 1, computing device 104 may develop ration program 136 as a function of edible 132 and intended functional goal using a ration machine-learning model. As used in this disclosure a "ration machine-learning model" is a machine-learning model to produce a ration program output given edibles and/or intended functional goals as inputs; this is in contrast to a non-machine learning software program where the commands to be executed are determined in advance by a user and written in a programming language. Ration machine-learning model may include one or more ration machine-learning processes such as supervised, unsupervised, or reinforcement machine-learning processes that computing device 104 and/or a remote device may or may not use in the development of ration program 136. Ration machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train ration machine-learning process as a function of a ration training set. As used in this disclosure a "ration training set" is a training set that correlates an intended functional goal to an edible. The ration training set may be received as a function of user-entered edibles, intended functional goals, and/or ration programs. For example, and without limitation, an intended functional goal of treating post traumatic stress disorder may correlate to an edible of blueberries. Computing device 104 may receive ration training by receiving correlations of intended functional goals and/or edibles that were previously received and/or determined during a previous iteration of developing ration programs. The ration training set may be received by one or more remote devices that at least correlate an intended functional goal and/or edible to a ration program, wherein a remote device is an external device to computing device 104, as described above. Ration training set may be received in the form of one or more user-entered correlations of an intended functional goal and/or edible to a ration program. Additionally or alternatively, a user may include an informed advisor, wherein an informed advisor may include, without limitation psychiatrists, psychologists, endocrinologist, psychotherapists, family physicians, gastroenterologists, internists, oncologists, pediatricians, cardiologists, geneticists, neurologists, physical therapists, primary care providers, and the like thereof.

Still referring to FIG. 1, computing device 104 may receive ration machine-learning model from the remote device that utilizes one or more ration machine learning processes, wherein a remote device is described above in detail. For example, and without limitation, a remote device may include a computing device, external device, processor, and the like thereof. The remote device may perform the ration machine-learning process using the ration training set to develop ration program 136 and transmit the output to computing device 104. The remote device may transmit a signal, bit, datum, or parameter to computing device 104 that at least relates to ration program 136. Additionally or alternatively, the remote device may provide an updated machine-learning model. For example, and without limitation, an updated machine-learning model may be comprised of a firmware update, a software update, a ration machine-learning process correction, and the like thereof. As a non-limiting example a software update may incorporate a new intended functional goal that relates to a modified edible. Additionally or alternatively, the updated machine learning model may be transmitted to the remote device, wherein the remote device may replace the ration machine-learning model with the updated machine-learning model and develop the ration program as a function of the intended functional goal using the updated machine-learning model. The updated machine-learning model may be transmitted by the remote device and received by computing device 104 as a software update, firmware update, or corrected ration machine-learning model. For example, and without limitation ration machine-learning model may utilize a neural net machine-learning process, wherein the updated machine-learning model may incorporate decision tree machine-learning processes. Updated machine learning model may additionally or alternatively include any machine-learning model used as an updated machine learning model as described in U.S. Nonprovisional application Ser. No. 17/106,658, the entirety of which is incorporated herein by reference.

Figure 2:
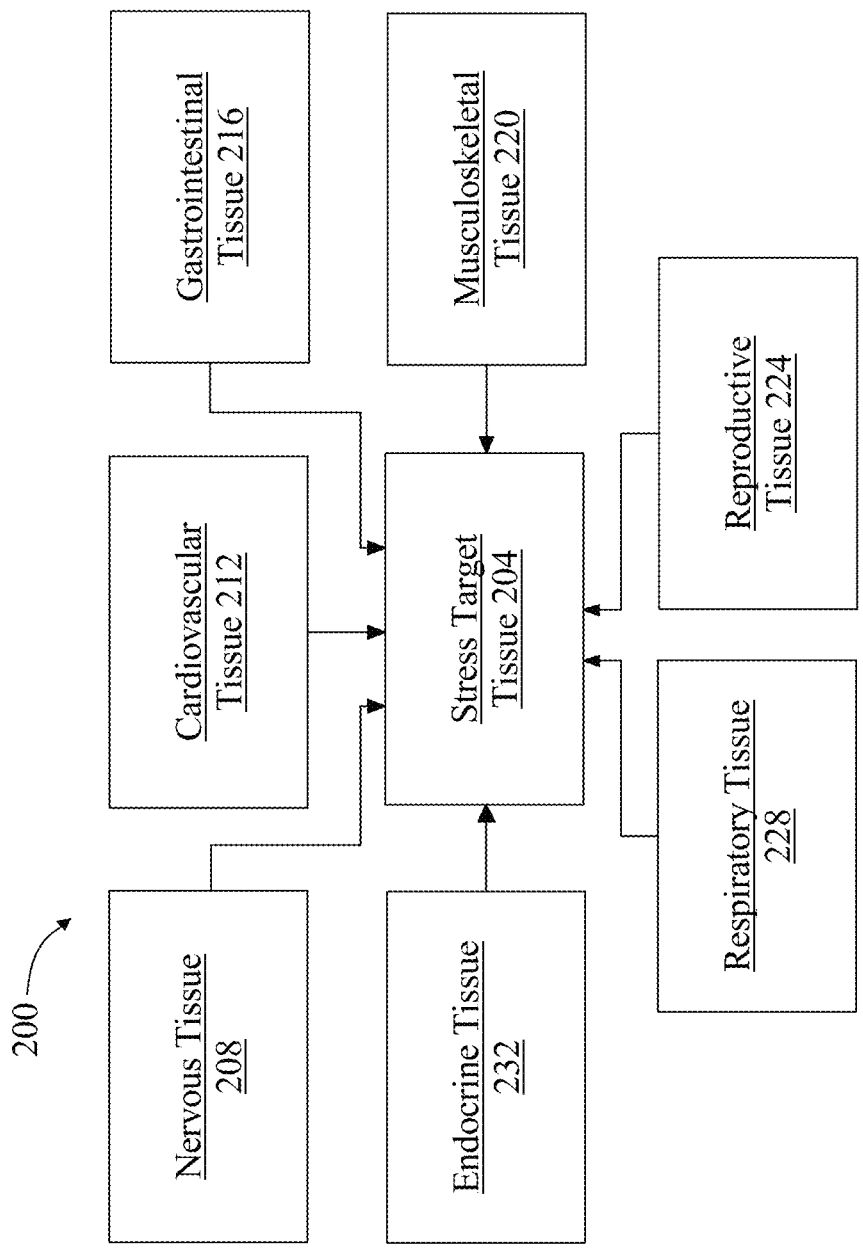
FIG. 2 is a block diagram illustrating an exemplary embodiment of a stress target tissue.

Now referring to FIG. 2, an exemplary embodiment 200 of a stress target tissue 204 is illustrated. As used in this disclosure a "stress target tissue" is one or more tissues and/or cells that are affected by a stressor. For example, and without limitation, stress target tissue may include cells, tissues, organs, and the like thereof of the human body. In an embodiment, stress target tissue 204 may include nervous tissue 208. As used in this disclosure "nervous tissue" is a cell and/or group of cells that are associated with the transmission of electrical signals along a membrane and/or chemical signals across a synaptic gap in the human body. For example, and without limitation, nervous tissue 208 may include one or more tissues such as the brain, spinal cord, neurons, neuroglia, and the like thereof. In an embodiment, stress target tissue 204 may include cardiovascular tissue 212. As used in this disclosure "cardiovascular tissue" is a cell and/or group of cells that are associated with the circulation of blood in the body. For example, and without limitation, cardiovascular tissue 212 may include one or more tissues such as the heart, cardiac muscle, specialized conductive tissue, valves, blood vessels, connective tissue, and the like thereof. In an embodiment, stress target tissue 204 may include gastrointestinal tissue 216. As used in this disclosure "gastrointestinal tissue" is a cell and/or group of cells that are associated with the ingestion, digestion, and/or absorption of nutrients. For example, and without limitation, gastrointestinal tissue 216 may include one or more tissues such as the esophagus, stomach, bowel, mucosa, submucosa, muscular tissue, serosa, adventitia, and the like thereof.

Still referring to FIG. 2, stress target tissue 204 may include musculoskeletal tissue 220. As used in this disclosure "musculoskeletal tissue" is a cell and/or group of cells that are associated with the support of the body, motion of the body, and/or protection of vital organs. For example, and without limitation, musculoskeletal tissue 220 may include one or more tissues such as bones, muscles, cartilage, tendons, ligaments, joints, connective tissue, and the like thereof. In an embodiment, stress target tissue 204 may include reproductive tissue 224. As used in this disclosure "reproductive tissue" is a cell and/or group of cells that are associated with procreation. For example, and without limitation, reproduction tissue 224 may include one or more tissues such as the testes, seminal vesicles, prostate gland, bulbourethral gland, ovaries, uterus, oviducts, and the like thereof. In an embodiment, stress target tissue 204 may include respiratory tissue 228. As used in this disclosure "respiratory tissue" is a cell and/or group of cells that are associated with the external exchange of gases. For example, and without limitation, respiratory tissue 228 may include one or more tissues such as the mouth, nose, sinuses, pharynx, trachea, bronchial tubes, lungs, diaphragm, alveoli, bronchioles, lung lobes, pleura, cilia, epiglottis, larynx, and the like thereof. In an embodiment, stress target tissue 204 may include endocrine tissue 232. As used in this disclosure "endocrine tissue" is a cell and/or group of cells that are associated with the control of mood, growth, metabolism, and/or reproduction. For example, and without limitation, endocrine tissue 232 may include one or more tissues such as the hypothalamus, pituitary gland, thyroid gland, parathyroid gland, adrenal gland, pineal body, ovaries, testes, and the like thereof.

Figure 3:
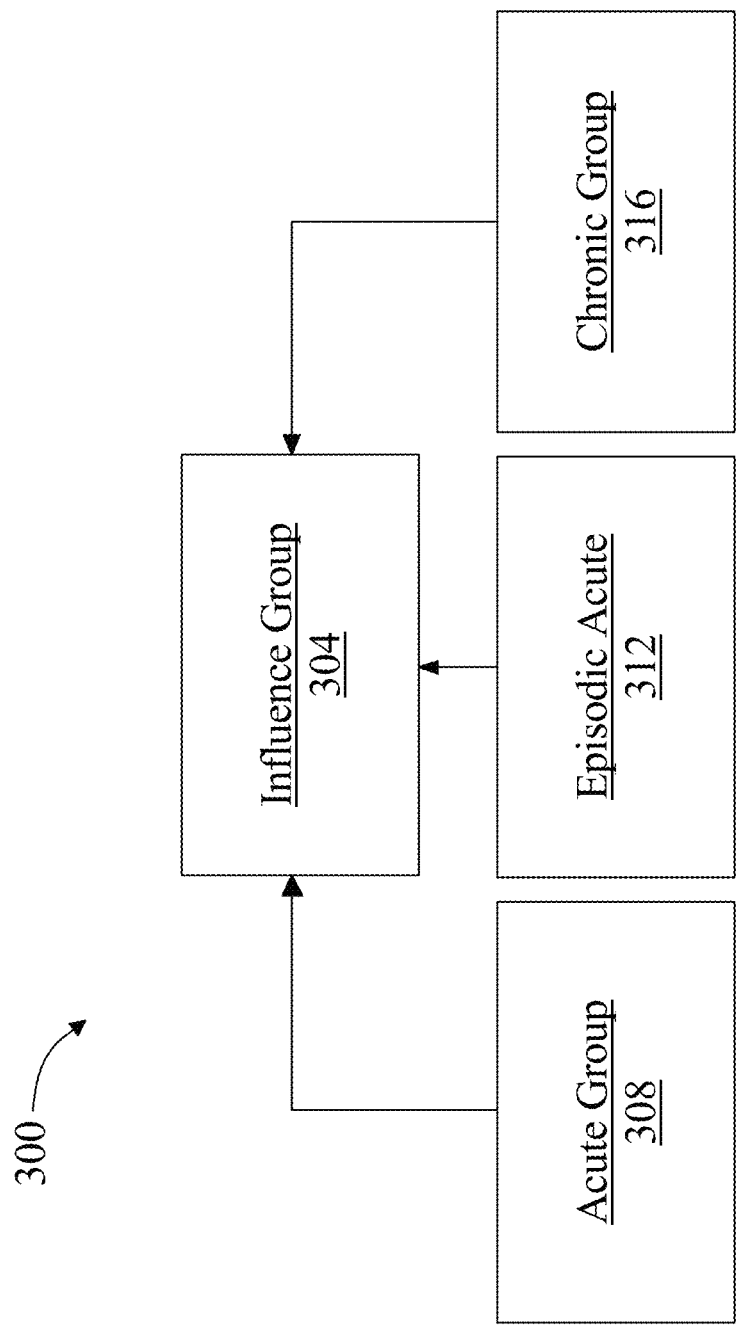
FIG. 3 is a block diagram illustrating an exemplary embodiment of an influence group.

Now referring to FIG. 3, an exemplary embodiment 300 of an influence group 304 is illustrated. As used in this disclosure an "influence group" is a group representing one or more types of influences that effect the individual's body. In an embodiment influence group 304 may include an acute group 308. As used in this disclosure an "acute group" is a group representing an influence that effects the body of an individual for a short period of time. For example, and without limitation, acute group 308 may include influences that result from single stressor, wherein the physiological influence effects the individual's body for up to 30 days. As a further non-limiting example, acute group 308 may include one or more influences such as, but not limited to, emotional unresponsiveness, dissociation from reality, amnesia, flashbacks, anxiety, sleeplessness, irritability, and the like thereof. In an embodiment influence group 304 may include an episodic acute group 312. As used in this disclosure an "episodic acute group" is a group representing an influence that effects the body of an individual disproportionately to the stressor. For example, and without limitation, episodic acute group 312 may denote influences such as, but not limited to, irritability, rapid heartbeat, panic attacks, heartburn, muscular pain, heart disease, hypertension, and the like thereof. As a further non-limiting example, episodic acute group 312 may include an influence such as a panic attack, wherein the stressor is dropping an object on the floor. In an embodiment influence group 304 may include a chronic group 316. As used in this disclosure a "chronic group" is a group representing an influence that effects the body of an individual for prolonged periods of time. For example, and without limitation, chronic group 316 may include one or more groups of influences as a result of a high-pressure job, consistent relationship problem, numerous financial difficulties, and the like thereof. As a further non-limiting example, chronic group 316 may include one or more groups of influences such as, but not limited to, unusual irritability, difficulty concentrating, reduced appetite, sleeplessness, anxiety disorders, heart disease, weight gain, memory disorders, depression, digestive disorders, and the like thereof.

Figure 4:
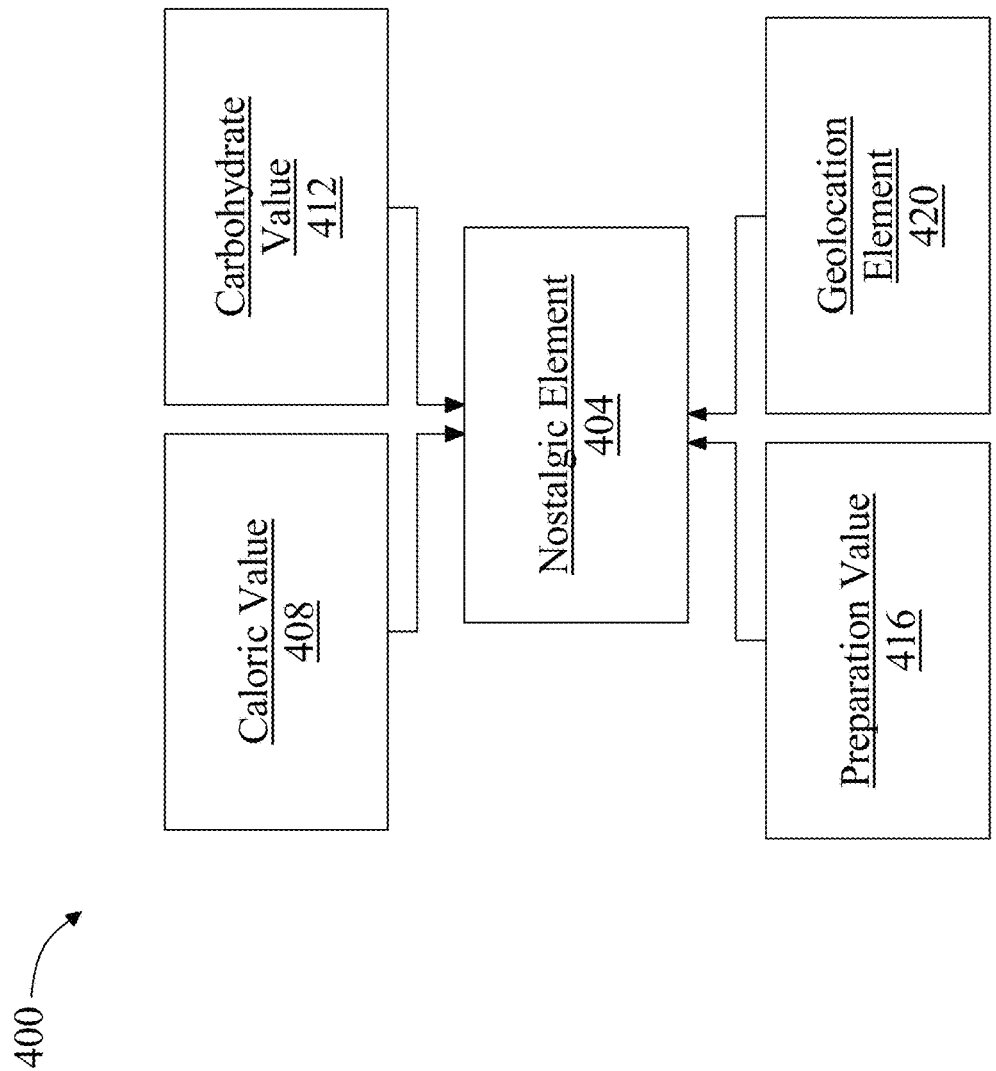
FIG. 4 is a block diagram illustrating an exemplary embodiment of a nostalgic element.

Now referring to FIG. 4, an exemplary embodiment 400 of a nostalgic element 404 is illustrated. As used in this disclosure a "nostalgic element" is an element of datum representing a soothing and/or comforting effect of an edible. For example, and without limitation, nostalgic element 404 may include one or more comforting effects that aid in reducing negative emotions of an individual. As a further non-limiting example, nostalgic element 404 may include one or more soothing effects to alter an individual's mood. As a further non-limiting example, nostalgic element 404 may include one or more elements that a user may previously have received a benefit from. In an embodiment, nostalgic element 404 may include a caloric value 408. As used in this disclosure a "caloric value" is a measurable value associated with the magnitude of the units of energy in an edible. For example, and without limitation, caloric value 408 may be 899 calories for a cup of milk chocolate. As a further non-limiting example, caloric value 408 may be 99 calories for a mini cauliflower pizza. As a further non-limiting example, caloric value 408 may be 220 calories for a cup of ice cream. In an embodiment, nostalgic element 404 may include a carbohydrate value 412. As used in this disclosure a "carbohydrate value" is measurable value associated with the magnitude of carbohydrates in an edible. For example, and without limitation, carbohydrate value 412 may be 80 grams of carbohydrates for a soft pretzel. As a further non-limiting example, carbohydrate value 412 may be 4 grams of carbohydrates for cauliflower macaroni and cheese. As a further non-limiting example, carbohydrate value 412 may be 30 grams of carbohydrates for a doughnut. In an embodiment, and without limitation, nostalgic element 404 may include a preparation value 420. As used in this disclosure a "preparation value" is a value representing a time period required to prepare and/or cook an edible, wherein a time period includes a measurement of time such as, but not limited to, seconds, minutes, hours, days, weeks, months, years, and the like thereof. For example and without limitation, preparation value 416 may include a value of 20 minutes to prepare a pizza. As a further non-limiting example, preparation value 416 may include a value of 45 seconds for keto ice cream. As a further non-limiting example, preparation value 416 may be 2 hours for an apple pie. In an embodiment, and without limitation, nostalgic element 404 may include a geolocation element 420. As used in this disclosure a "geolocation element" is an element of datum representing one or more soothing edibles associated with a region and/or nationality. For example, and without limitation, geolocation element 420 may include an element of datum representing one or more soothing edibles as a function of a region such as, but not limited to, Afghanistan, Australia, New Zealand, Canada, Egypt, France, Hong Kong, India, Indonesia, Italy, Philippines, Poland, Puerto Rico, Russia, Spain, Taiwan, Turkey, United Kingdom, United States, and the like thereof. As a further non-limiting example, geolocation element 420 may denote that an edible of cheesecake may have a soothing effect for an individual in Canada, wherein geolocation element 420 may denote that an edible of Kushari may have a soothing effect for an individual in Egypt.

Figure 5:
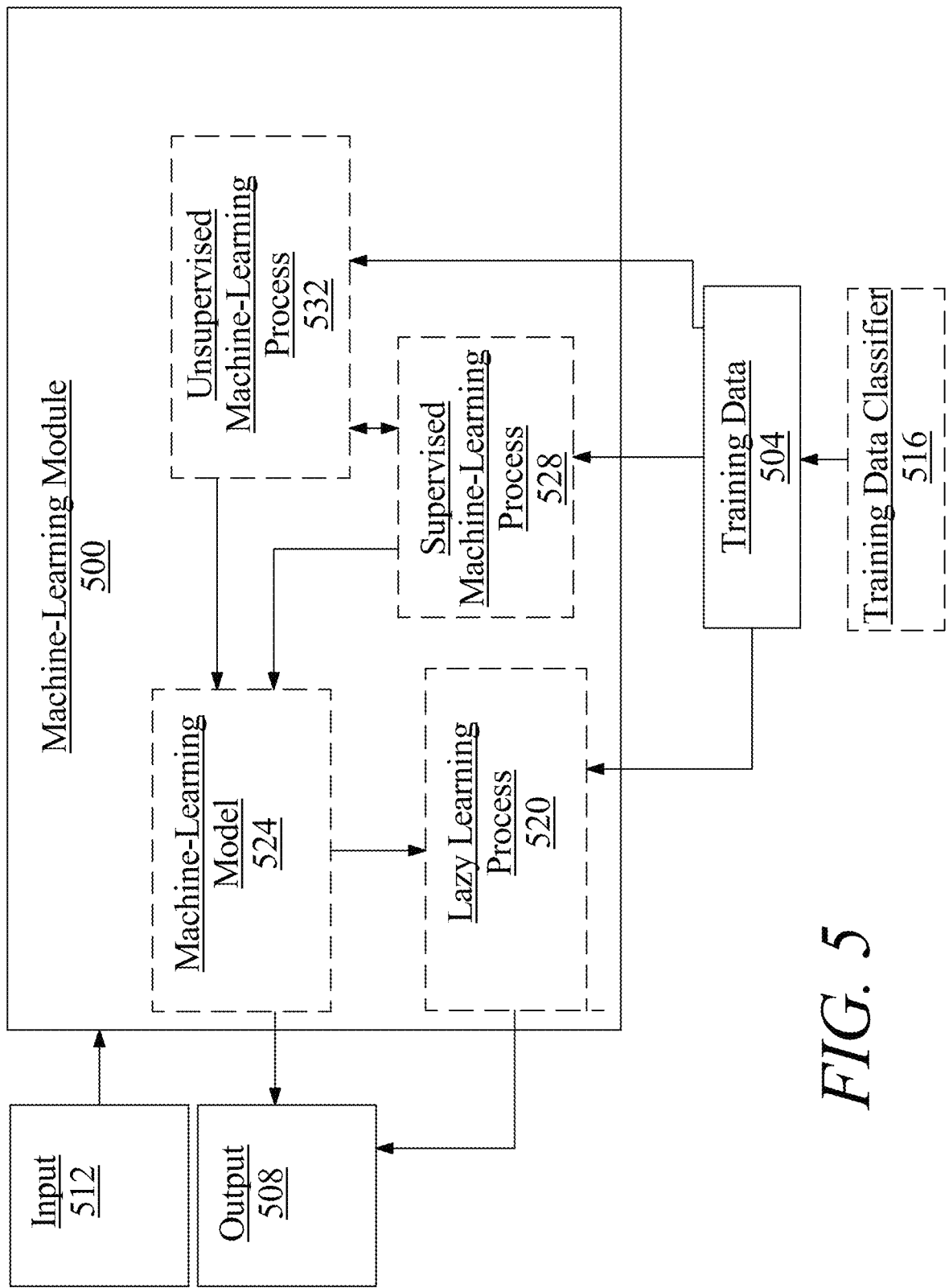
FIG. 5 is a block diagram of an exemplary embodiment of a machine-learning module.

Referring now to FIG. 5, an exemplary embodiment of a machine-learning module 500 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 504 to generate an algorithm that will be performed by a computing device/module to produce outputs 508 given data provided as inputs 512; this is in contrast to a non-machine learning software program where the commands to be executed are determined in advance by a user and written in a programming language.

Still referring to FIG. 5, "training data," as used herein, is data containing correlations that a machine-learning process may use to model relationships between two or more categories of data elements. For instance, and without limitation, training data 504 may include a plurality of data entries, each entry representing a set of data elements that were recorded, received, and/or generated together; data elements may be correlated by shared existence in a given data entry, by proximity in a given data entry, or the like. Multiple data entries in training data 504 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 504 according to various correlations; correlations may indicate causative and/or predictive links between categories of data elements, which may be modeled as relationships such as mathematical relationships by machine-learning processes as described in further detail below. Training data 504 may be formatted and/or organized by categories of data elements, for instance by associating data elements with one or more descriptors corresponding to categories of data elements. As a non-limiting example, training data 504 may include data entered in standardized forms by persons or processes, such that entry of a given data element in a given field in a form may be mapped to one or more descriptors of categories. Elements in training data 504 may be linked to descriptors of categories by tags, tokens, or other data elements; for instance, and without limitation, training data 504 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 5, training data 504 may include one or more elements that are not categorized; that is, training data 504 may not be formatted or contain descriptors for some elements of data. Machine-learning algorithms and/or other processes may sort training data 504 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 504 to be made applicable for two or more distinct machine-learning algorithms as described in further detail below. Training data 504 used by machine-learning module 500 may correlate any input data as described in this disclosure to any output data as described in this disclosure. As a non-limiting illustrative example inputs comprising stress representations and/or relative vectors may result in an equanimity signature output.

Further referring to FIG. 5, training data may be filtered, sorted, and/or selected using one or more supervised and/or unsupervised machine-learning processes and/or models as described in further detail below; such models may include without limitation a training data classifier 516. Training data classifier 516 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 500 may generate a classifier using a classification algorithm, defined as a processes whereby a computing device and/or any module and/or component operating thereon derives a classifier from training data 504. Classification may be performed using, without limitation, linear classifiers such as without limitation logistic regression and/or naïve Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 516 may classify elements of training data to relative vectors associated with one or more acclimation elements.

Still referring to FIG. 5, machine-learning module 500 may be configured to perform a lazy-learning process 520 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 504. Heuristic may include selecting some number of highest-ranking associations and/or training data 504 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 5, machine-learning processes as described in this disclosure may be used to generate machine-learning models 524. A "machine-learning model," as used in this disclosure, is a mathematical and/or algorithmic representation of a relationship between inputs and outputs, as generated using any machine-learning process including without limitation any process as described above, and stored in memory; an input is submitted to a machine-learning model 524 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 524 may be generated by creating an artificial neural network, such as a convolutional neural network comprising an input layer of nodes, one or more intermediate layers, and an output layer of nodes. Connections between nodes may be created via the process of "training" the network, in which elements from a training data 504 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 5, machine-learning algorithms may include at least a supervised machine-learning process 528. At least a supervised machine-learning process 528, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include stress representations and/or relative vectors as described above as inputs, equanimity signatures as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 504. Persons skilled in the art, upon reviewing the entirety of this disclosure, will be aware of various possible variations of at least a supervised machine-learning process 528 that may be used to determine relation between inputs and outputs. Supervised machine-learning processes may include classification algorithms as defined above.

Further referring to FIG. 5, machine learning processes may include at least an unsupervised machine-learning processes 532. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 5, machine-learning module 500 may be designed and configured to create a machine-learning model 524 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 5, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Figure 6:
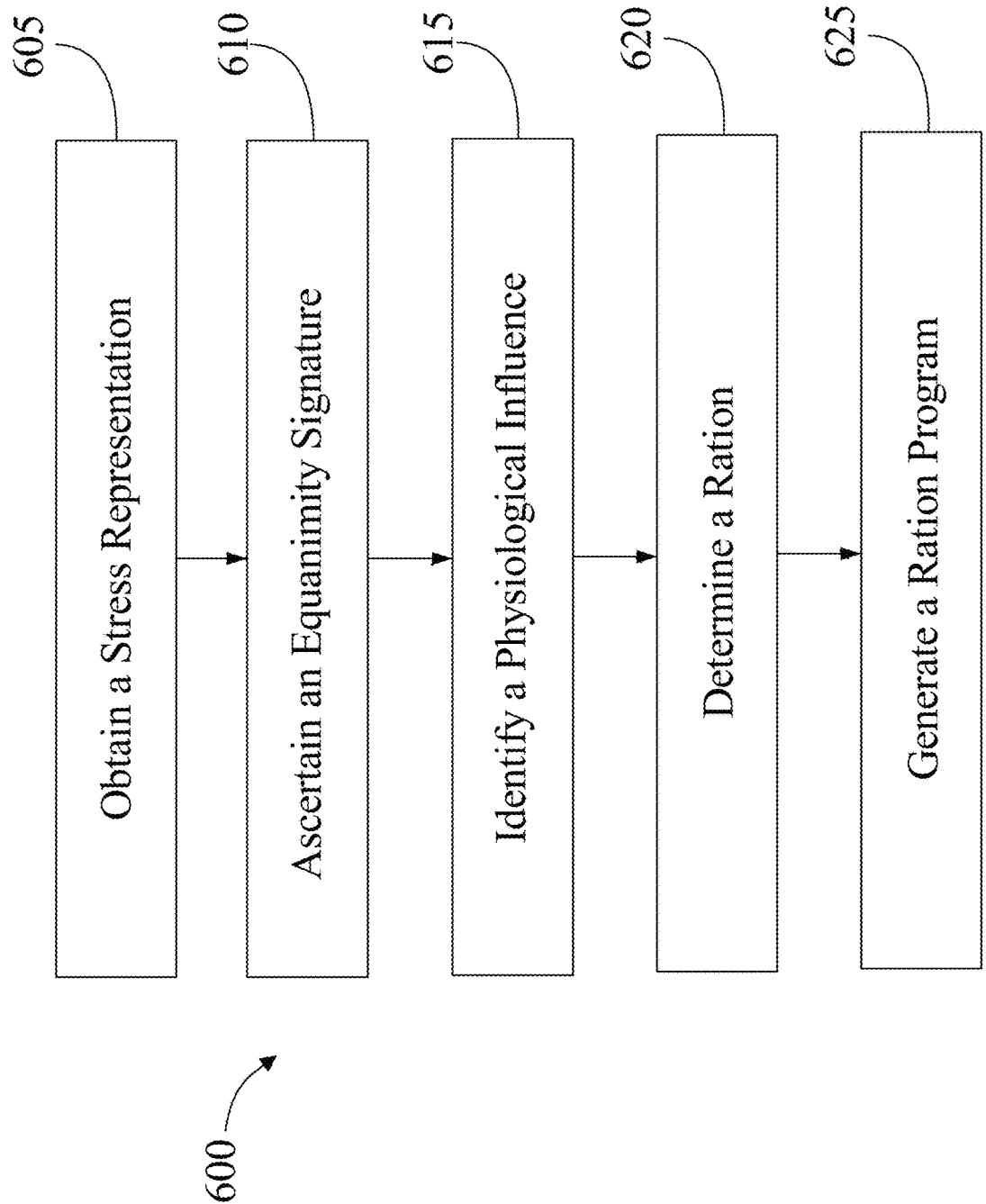
FIG. 6 is a process flow diagram illustrating an exemplary embodiment of a method for generating a stress disorder ration program.

Now referring to FIG. 6, an exemplary embodiment 600 of a method for generating a stress disorder ration program is illustrated. At step 605, a computing device 104 obtains a stress representation 108. Computing device 104 includes any of the computing device 104 as described above, in reference to FIGS. 1-5. Stress representation 108 includes any of the stress representation 108 as described above, in reference to FIGS. 1-5.

Still referring to FIG. 6, at step 610, computing device 104 ascertains an equanimity signature 112. Equanimity signature 112 includes any of the equanimity signature 112 as described above, in reference to FIGS. 1-5. Computing device 104 ascertains equanimity signature 112 by retrieving an acclimation element 116. Acclimation element 116 includes any of the acclimation element 116 as described above, in reference to FIGS. 1-5. Computing device 104 determines a relative vector 120 as a function of acclimation element 116. Relative vector 120 includes any of the relative vector 120 as described above, in reference to FIGS. 1-5. Computing device 104 ascertains equanimity signature 112 as a function of relative vector 120 and stress representation 108 using a stress machine-learning model 124. Stress machine-learning model 124 includes any of the stress machine-learning model 124 as described above, in reference to FIGS. 1-5.

Still referring to FIG. 6, at step 615, computing device 104 identifies a physiological influence 128 as a function of equanimity signature 112. Physiological influence 128 includes any of the physiological influence 128 as described above, in reference to FIGS. 1-5.

Still referring to FIG. 6, at step 620, computing device 104 determines an edible 132 as a function of physiological influence 128. Edible 132 includes any of the edible 132 as described above, in reference to FIGS. 1-5.

Still referring to FIG. 6, at step 625, computing device 104 generates a ration program 136. Ration program 136 includes any of the ration program 136 as described above, in reference to FIGS. 1-5.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 7:
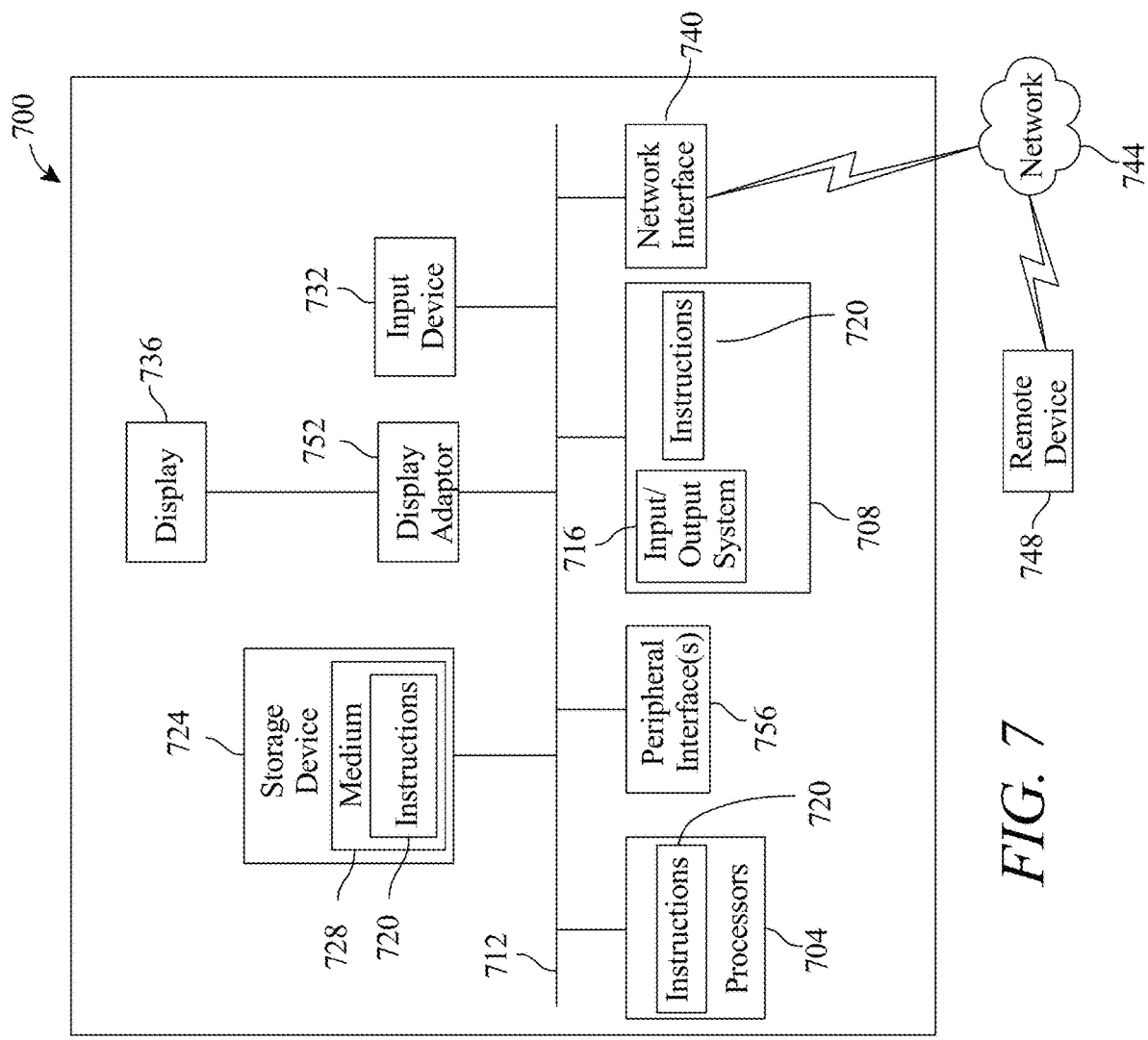
FIG. 7 is a block diagram of a computing system that can be used to implement any one or more of the methodologies disclosed herein and any one or more portions thereof.

FIG. 7 shows a diagrammatic representation of one embodiment of a computing device in the exemplary form of a computer system 700 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 700 includes a processor 704 and a memory 708 that communicate with each other, and with other components, via a bus 712. Bus 712 may include any of several types of bus structures including, but not limited to, a memory bus, a memory controller, a peripheral bus, a local bus, and any combinations thereof, using any of a variety of bus architectures.

Processor 704 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 704 may be organized according to Von Neumann and/or Harvard architecture as a non-limiting example. Processor 704 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC).

Memory 708 may include various components (e.g., machine-readable media) including, but not limited to, a random-access memory component, a read only component, and any combinations thereof. In one example, a basic input/output system 716 (BIOS), including basic routines that help to transfer information between elements within computer system 700, such as during start-up, may be stored in memory 708. Memory 708 may also include (e.g., stored on one or more machine-readable media) instructions (e.g., software) 720 embodying any one or more of the aspects and/or methodologies of the present disclosure. In another example, memory 708 may further include any number of program modules including, but not limited to, an operating system, one or more application programs, other program modules, program data, and any combinations thereof.

Computer system 700 may also include a storage device 724. Examples of a storage device (e.g., storage device 724) include, but are not limited to, a hard disk drive, a magnetic disk drive, an optical disc drive in combination with an optical medium, a solid-state memory device, and any combinations thereof. Storage device 724 may be connected to bus 712 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 724 (or one or more components thereof) may be removably interfaced with computer system 700 (e.g., via an external port connector (not shown)). Particularly, storage device 724 and an associated machine-readable medium 728 may provide nonvolatile and/or volatile storage of machine-readable instructions, data structures, program modules, and/or other data for computer system 700. In one example, software 720 may reside, completely or partially, within machine-readable medium 728. In another example, software 720 may reside, completely or partially, within processor 704.

Computer system 700 may also include an input device 732. In one example, a user of computer system 700 may enter commands and/or other information into computer system 700 via input device 732. Examples of an input device 732 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 732 may be interfaced to bus 712 via any of a variety of interfaces (not shown) including, but not limited to, a serial interface, a parallel interface, a game port, a USB interface, a FIREWIRE interface, a direct interface to bus 712, and any combinations thereof. Input device 732 may include a touch screen interface that may be a part of or separate from display 736, discussed further below. Input device 732 may be utilized as a user selection device for selecting one or more graphical representations in a graphical interface as described above.

A user may also input commands and/or other information to computer system 700 via storage device 724 (e.g., a removable disk drive, a flash drive, etc.) and/or network interface device 740. A network interface device, such as network interface device 740, may be utilized for connecting computer system 700 to one or more of a variety of networks, such as network 744, and one or more remote devices 748 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 744, may employ a wired and/or a wireless mode of communication. In general, any network topology may be used. Information (e.g., data, software 720, etc.) may be communicated to and/or from computer system 700 via network interface device 740.

Computer system 700 may further include a video display adapter 752 for communicating a displayable image to a display device, such as display device 736. Examples of a display device include, but are not limited to, a liquid crystal display (LCD), a cathode ray tube (CRT), a plasma display, a light emitting diode (LED) display, and any combinations thereof. Display adapter 752 and display device 736 may be utilized in combination with processor 704 to provide graphical representations of aspects of the present disclosure. In addition to a display device, computer system 700 may include one or more other peripheral output devices including, but not limited to, an audio speaker, a printer, and any combinations thereof. Such peripheral output devices may be connected to bus 712 via a peripheral interface 756. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve systems and methods according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for generating a stress disorder ration program, the system comprising:
   a biological sampling device configured to collect a biological sample from an individual; and
   a computing device, the computing device configured to:
   obtain a stress representation;
   ascertain an equanimity signature based on the biological sample, wherein ascertaining the equanimity signature further comprises:
   retrieving an acclimation element;
   determining a relative vector as a function of the acclimation element;
   creating a stress training set by correlating one or more valuations of equanimity signatures to one or more valuations of relative vectors;
   training a stress machine-learning model on the stress training set and computing an expected loss as an error function, wherein the stress machine-learning model is a neural network; and ascertaining the equanimity signature by inputting the relative vector into the trained stress machine-learning model and receiving the equanimity signature as an output of the trained stress machine-learning model;

identify a physiological influence as a function of the equanimity signature;

determine an edible as a function of the physiological influence and an edible machine-learning model; and generate a ration program as a function of the edible, wherein generating the ration program comprises utilizing a ration machine-learning model, wherein utilizing the ration machine-learning model comprises:

generating, the ration machine-learning model;

transmitting, to a remote device, the ration machine-learning model;

generating, by the remote device, an updated ration machine-learning model;

transmitting, to the computing device, the updated ration machine-learning model;

receiving, from a remote device, a ration training set, wherein the ration training set comprises edibles correlated to ration programs, wherein the ration training set is received from previous iterations of the ration machine-learning model;

training the updated ration machine-learning model as a function the ration training set; and generating the ration program as a function of the trained updated ration machine-learning model.

2. The system of claim 1, wherein the stress representation includes a psychological analysis.

3. The system of claim 1, wherein obtaining the stress representation further comprises retrieving a behavior pattern and obtaining the stress representation as a function of the behavior pattern.

4. The system of claim 3, wherein the behavior pattern includes a stress mitigator.

5. The system of claim 1, wherein ascertaining the equanimity signature further comprises identifying a likelihood element and ascertaining the equanimity signature as a function of the likelihood element.

6. The system of claim 1, wherein determining the relative vector further comprises:

retrieving an expected response; and determining the relative vector as a function of the acclimation element and the expected response using a relative machine-learning model.

7. The system of claim 1, wherein ascertaining the equanimity signature includes determining a stress disorder and producing the equanimity signature as a function of the stress disorder.

8. The system of claim 1, wherein identifying the physiological influence further comprises:

retrieving at least a stress target tissue; and identifying the physiological influence as a function of the stress target tissue and equanimity signature using a physiological machine-learning model.

9. The system of claim 1, wherein identifying the physiological influence further comprises determining an influence group and identifying the physiological influence as a function of the influence group.

10. The system of claim 1, wherein determining the edible further comprises identifying at least a nostalgic element and determining the edible as a function of the nostalgic element.

11. A method for generating a stress disorder ration program, the method comprising:

collecting, using a biological sampling device, a biological sample from an individual;

obtaining, by a computing device, a stress representation;

ascertaining, by the computing device, an equanimity signature based on the biological sample, wherein ascertaining the equanimity signature further comprises:

retrieving an acclimation element;

determining a relative vector as a function of the acclimation element;

creating a stress training set by correlating one or more valuations of equanimity signatures to one or more valuations of relative vectors;

training a stress machine-learning model on the stress training set and computing an expected loss as an error function, wherein the stress-machine-learning model is a neural network; and ascertaining the equanimity signature by inputting the relative vector into the trained stress machine-learning model and receiving the equanimity signature as an output of the trained stress machine-learning model;

identifying, by the computing device, a physiological influence as a function of the equanimity signature;

determining, by the computing device, an edible as a function of the physiological influence and an edible machine-learning model; and generating, by the computing device, a ration program as a function of the edible, wherein generating the ration program comprises utilizing a ration machine-learning model, wherein utilizing the ration machine-learning model comprises:

generating, the ration machine-learning model;

transmitting, to a remote device, the ration machine-learning model;

generating, by the remote device, an updated ration machine-learning model;

transmitting, to the computing device, the updated ration machine-learning model;

receiving, from a remote device, a ration training set, wherein the ration training set comprises edibles correlated to ration programs, wherein the ration training set is received from previous iterations of the ration machine-learning model;

training the updated ration machine-learning model as a function the ration training set; and generating the ration program as a function of the trained updated ration machine-learning model.

12. The method of claim 11, wherein the stress representation includes a psychological analysis.

13. The method of claim 11, wherein obtaining the stress representation further comprises retrieving a behavior pattern and obtaining the stress representation as a function of the behavior pattern.

14. The method of claim 13, wherein the behavior pattern includes a stress mitigator.

15. The method of claim 11, wherein ascertaining the equanimity signature further comprises identifying a likelihood element and ascertaining the equanimity signature as a function of the likelihood element.

16. The method of claim 11, wherein determining the relative vector further comprises:

retrieving an expected response; and determining the relative vector as a function of the acclimation element and the expected response using a relative machine-learning model.

17. The method of claim 11, wherein ascertaining the equanimity signature includes determining a stress disorder and producing the equanimity signature as a function of the stress disorder.

18. The method of claim 11, wherein identifying the physiological influence further comprises:
   retrieving at least a stress target tissue; and
   identifying the physiological influence as a function of the stress target tissue and equanimity signature using a physiological machine-learning model.

19. The method of claim 11, wherein identifying the physiological influence further comprises determining an influence group and identifying the physiological influence as a function of the influence group.

20. The method of claim 11, wherein determining the edible further comprises identifying at least a nostalgic element and determining the edible as a function of the nostalgic element.

* * * * *